US00PP36994P2

(12) United States Plant Patent
Meilland

(10) Patent No.: US PP36,994 P2
(45) Date of Patent: Oct. 7, 2025

(54) GROUND COVER ROSE PLANT NAMED 'MEIDELVEGA'

(50) Latin Name: *Rosa hybrida*
Varietal Denomination: MEIDELVEGA

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 19/063,649

(22) Filed: Feb. 26, 2025

(30) Foreign Application Priority Data

Jan. 13, 2025 (QZ) ..... PBR 2025/0089

(51) Int. Cl.
*A01H 5/02* (2018.01)
*A01H 6/74* (2018.01)

(52) U.S. Cl.
USPC ..... Plt./101
CPC ..... *A01H 6/749* (2018.05); *A01H 5/02* (2013.01)

(58) Field of Classification Search
USPC ..... Plt./101
See application file for complete search history.

(56) References Cited

U.S. PATENT DOCUMENTS

PP17,877 P3 * 7/2007 Meilland ..... A01H 5/02 Plt./108
PP28,541 P3 10/2017 Meilland

* cited by examiner

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of ground cover rose plant, referred to by its cultivar name, 'MEIDELVEGA', is described. The new variety forms in abundance on a nearly continuous basis, velvet red colored blossoms. The growth habit is bushy. Dense, glossy, dark green colored ornamental foliage is formed. Additionally, the new variety is particularly well suited for growing as ornamentation in the landscape.

1 Drawing Sheet

Latin name of genus and species of plant claimed: *Rosa hybrida.*
Variety denomination: 'MEIDELVEGA'.

CROSS REFERENCE TO RELATED APPLICATIONS

This application claims priority to Plant Breeders' Right Application No. 2025/0089, which was filed at Community Plant Variety Office in the European Union on Jan. 13, 2025, the contents of which are hereby incorporated by reference for all purposes.

STATEMENT REGARDING PRIOR DISCLOSURES BY THE INVENTOR

The first sale or offer for sale of the new variety was Mar. 4, 2024, in Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior to the effective filing date of this application, and such sale or disclosure within one year was either derived directly or indirectly from the inventor.

BACKGROUND OF THE INVENTION

The new variety of ground cover rose plant of the present invention was created by controlled breeding during 2014, in Le Cannet de Maures, France by artificial pollination wherein two parents were crossed which previously had been studied in the hope that they would contribute the desired characteristics. The female parent (i.e., the seed parent) of the new variety an unnamed seedling that was the product of the cross between the 'MEINOIRAL' variety (not patented) and an unnamed seedling variety (not patented). The male parent (i.e., the pollen parent) of the new variety was the 'MEISCARLEBO' variety (U.S. Plant Pat. No. 28,541).

The parentage of the new variety can be summarized as follows:

('MEINOIRAL' x unnamed seedling) x 'MEISCARLEBO'

The seeds resulting from the above pollination were sown and small plants were obtained which were physically and biologically different from each other. Selective study resulted in the identification of a single plant of the new variety.

The new variety has been found to undergo asexual propagation in Le Cannet de Maures, France by a number of routes such as eye budding, softwood cuttings, and hardwood cuttings. Asexual propagation techniques in in Le Cannet de Maures, France, such as eye budding, softwood cuttings, and hardwood cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of ground cover rose plant of the present invention possesses the following combination of characteristics:

(a) forming velvet red colored blossoms, (b) providing single flowers, and (c) exhibiting a bushy growth habit.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays velvet red color flowers compared to the pink colored flowers of the unnamed seedling female parent (i.e., the product of ('MEINOIRAL' x unnamed seedling)). Additionally, the new variety exhibits a lower petal count compared to the 'MEISCARLEBO' variety (i.e., the pollen parent). Moreover, the new variety can be readily distinguished from non-parental related similar varieties. For example, the new variety has larger flowers with less petals compared to the 'MEIGALPIO' variety (U.S. Plant Pat. No. 17,877).

The new variety has been named the 'MEIDELVEGA' variety.

BRIEF DESCRIPTION OF THE PHOTOGRAPHS

The accompanying photograph shows, as nearly true as it is reasonably possible to make the same in a color illustration of this character, typical specimens of the plant parts of the new variety. The rose plants of the new variety were approximately one year of age and were observed during June while budded on 'Laxa' {unpatented} and growing outdoors at Le Cannet des Maures, Var, France. Dimensions in centimeters are indicated at the bottom of the photograph.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

Element 19—illustrates a specimen of a leaf with 9 leaflets—plan view—upper surface.

Element 20—illustrates a specimen of a leaf with 9 leaflets—plan view—under surface.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during June, while budded on its own roots and growing outdoors at Le Cannet des Maures, Var, France.

Botanical classification: *Rosa hybrida* cultivar 'MEIDELVEGA'.

Commercial classification: Ground Cover Rose.

Plant:

*Habit*.—Bushy.

*Height*.—Approximately 40.0 cm on average.

*Width*.—Approximately 60.0 cm on average.

Branches:

*Stem color*.—Old wood: Yellow-Green Group 146C. — young stems: A color between Green Group 143A and Yellow-Green Group 144A.

*Length*.—From the crown to the flower is typically between 25 cm to 40 cm.

*Diameter*.—Approximately 0.4 cm on average.

*Prickles*.—Configuration on adult stems: concave to upright, elongated and curved downwards on the upper surface and very concave on the under surface. — quantity: approximately 6 prickles on average per 10 cm long young stem and approximately 6 prickles on average per 10 cm long adult stem. — length: approximately 0.6 cm on young stems on average and approximately 0.8 cm on adult stems on average. — width at base: approximately 0.15 cm on young stems on average and approximately 0.2 cm on adult stems on average. — base shape: elliptical, very narrow, and short on young stem; elliptical, very narrow and long on adult stems. — color on young stems: a color between Yellow-Green Group 146D and Greyed-Yellow Group 160C. — color on adult stems: Greyed-Yellow Group 161B more or less suffused with Greyed-Orange Group 176C.

*Anthocyanin coloration of young shoots*.—Absent.

*Internode numbers on entire branch*.—Typically between 4 to 6.

*Internode length*.—Typically between 3.0 cm to 7.5 cm.

Leaflets:

*Number*.—3, 5, 7, and 9; most often 5.

*Shape*.—Tip: acuminate base: obtuse.

*Serration*.—Small and single.

*General appearance*.—Oval.

*Undulation*.—Very weak.

*Glossiness of upper side*.—Strong.

*Texture*.—Moderately leathery.

*Smoothness*.—Upper surface: smooth. — under surface: bumpy.

*Venation*.—Color is Yellow-Green Group 144C; and pattern is imparipinnate.

*Size*.—Terminal leaflet: length is typically between 5.5 cm and 8.0 cm; width is typically between 3.0 cm and 4.5 cm. — 5-Leaflet leaf. length is typically between 13.0 cm and 16.5 cm; width is typically between 9.0 cm and 12.5 cm.

Foliage:

*General appearance*.—Dense, darker with a glossy aspect.

*Young foliage*.—Upper surface color: a color between Green Group 137A and Yellow-Green Group 146A. — under surface color: A color between Green Group 137C and Yellow-Green Group 146C.

*Adult foliage*.—Upper surface color: A color between Green Group 139A and Yellow-Green Group 147A. — under surface color: A color between Yellow-Green Group 147A and Yellow-Green Group 147B.

*Petiole*.—Texture: upper surface is slightly tomentous and slightly glandular; under surface is slightly glandular. — length: typically between 2.0 cm and 4.0 cm. — width: approximately 1.0 cm on average. — upper surface color: Green Group 143A. — under surface color: Yellow-Green Group 144B.

*Rachis*.—Rachis length of terminal leaflet: typically between 4.0 cm to 5.5 cm. — rachis width of terminal leaflet: approximately 0.1 cm. — texture: upper surface is slightly tomentous; under surface is prickles. — upper surface color: Green Group 143A. — under surface color: Yellow-Green Group 144B.

*Stipules*.—Length: typically between 1.5 cm to 2.5 cm. — width: typically between 0.2 cm to 0.3 cm. — general appearance: rather broad and very serrated. — texture: smooth on upper and under surfaces. — upper surface color: Green Group 137A slightly suffused with Greyed Group 137A. — under surface color: Green Group 137B.

Inflorescence:

*Number of blossoms per stem*.—Typically 1 to 10 blooms per stem on average.

*Lastingness of the bloom*.—On the plant: approximately 10 days. — in vase: not tested.

*Bud*.—Shape: conical. — length: approximately 2.0 cm on average. — width: approximately 1.2 cm on average. — color as calyx breaks: upper surface: a color between Greyed-Purple Group 185A and Red Group 46A (velvety and bright); basal spot is very little and Yellow Group 9C. under surface: Red Group 53A; basal spot is very little and Yellow Group 9D.

*Sepals*.—Number: commonly 5. — length: typically between 2.0 cm and 2.5 cm. — width: typically between 0.5 cm and 0.6 cm. — shape: at the top: elongated and narrow. at the base: flat at union with the receptacle. — extensions: typically 3 sepals with no extension or very weak extensions, and 2 sepals with very weak extensions. — upper surface: texture: tomentous. color: Yellow-Green Group 144B completely covered with hairs near White Group 155A. — under surface: texture: tomentous and glandular. color: Yellow-Green Group 144B strongly suffused with Green Group 143A.

*Receptacle*.—Color: Yellow-Green Group 144A. — length: approximately 0.6 cm on average. — width: approximately 0.4 cm on average. — surface: tomentous. — shape: pyriform.

*Peduncle*.—Length: typically between 6.0 cm to 7.5 cm. — width: typically 0.1 cm to 0.2 cm. — surface: glandular. — color: Yellow-Green Group 144B.

*Flower*.—Diameter when open: approximately 6.8 cm on average. — depth of the flower: typically between 0.5 cm to 1.5 cm. — shape: flat cup shape. — shape when viewed from above: irregular rounded. — shape of the upper part of the flower profile: flattened convex. — shape of the lower part of the flower profile: flat. — type: single. — number of petals under normal conditions: typically between 5 and 7. — petals: shape: rounded (notched at the top and obtuse at the base). texture: semi-dry, thick. length: typically between 2.5 cm to 3.0 cm. width: typically between 2.5 cm to 3.5 cm. — undulation of the petal: medium. — reflexing of the petal: strong. — petal incision: very weak. — petal arrangement: imbricated with few petaloids (typically every third flower has one or two petaloids which look like smaller half petals). — petal drop: petals drop off cleanly before drying. — fragrance: none. — discoloration of the flower: no. — color when opening: basal spot on the upper surface: Yellow Group 8D. upper surface: Red Group 45A (intense velvety aspect). basal spot on the under surface: White Group 155B. under surface: Red Group 53C. — color of the open flower: basal spot on upper surface: White Group 155B. upper surface: a color which is Red Group 53A with a hint of Red-Purple Group 61B. basal spot on under surface: White Group 155B. under surface of the flower. a color between Red Group 53C and Red Group 53D. — anthers: approximately 100 on average, length is approximately 0.2 cm, width approximately 0.1 cm, coloration is Yellow Group 8B in the center and Yellow-Orange Group 17A on the edges, and arrangement is regular around styles. — filaments: length is typically between 0.2 cm to 0.5 cm; width is typically less than 0.1 cm; and coloration is Yellow Group 8B. — styles: length is typically between 0.6 cm to 0.8 cm, coloration is Yellow-Green Group 153C on the first half from the base and Red-Purple Group 60C on the second half to the top, and number is typically between 15 to 20. — stigmas: length is approximately 0.1 cm on average and coloration is Yellow-White Group 158A. — pollen: very abundant; color Orange Group 24A. — hips: not available.

Development:

*Vegetation*.—Strong.

*Blossoming*.—Abundant and nearly continuous early in the season from spring through frost; typically, in bloom outdoors from May to first frost in Le Cannet de Maures, France.

*Resistance to diseases*.—Very good tolerance against black spot (*Diplocarpon rosae*) and rust (*Phragmidium* sp.).

*Hardiness*.—Tested up to USDA Zone 5.

The new 'MEIDELVEGA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of ground cover rose plant named 'MEIDELVEGA' characterized by the following combination of characteristics:

(a) forming velvet red colored blossoms, (b) providing single flowers, and (c) exhibiting a bushy growth habit;

substantially as herein shown and described.

* * * * *

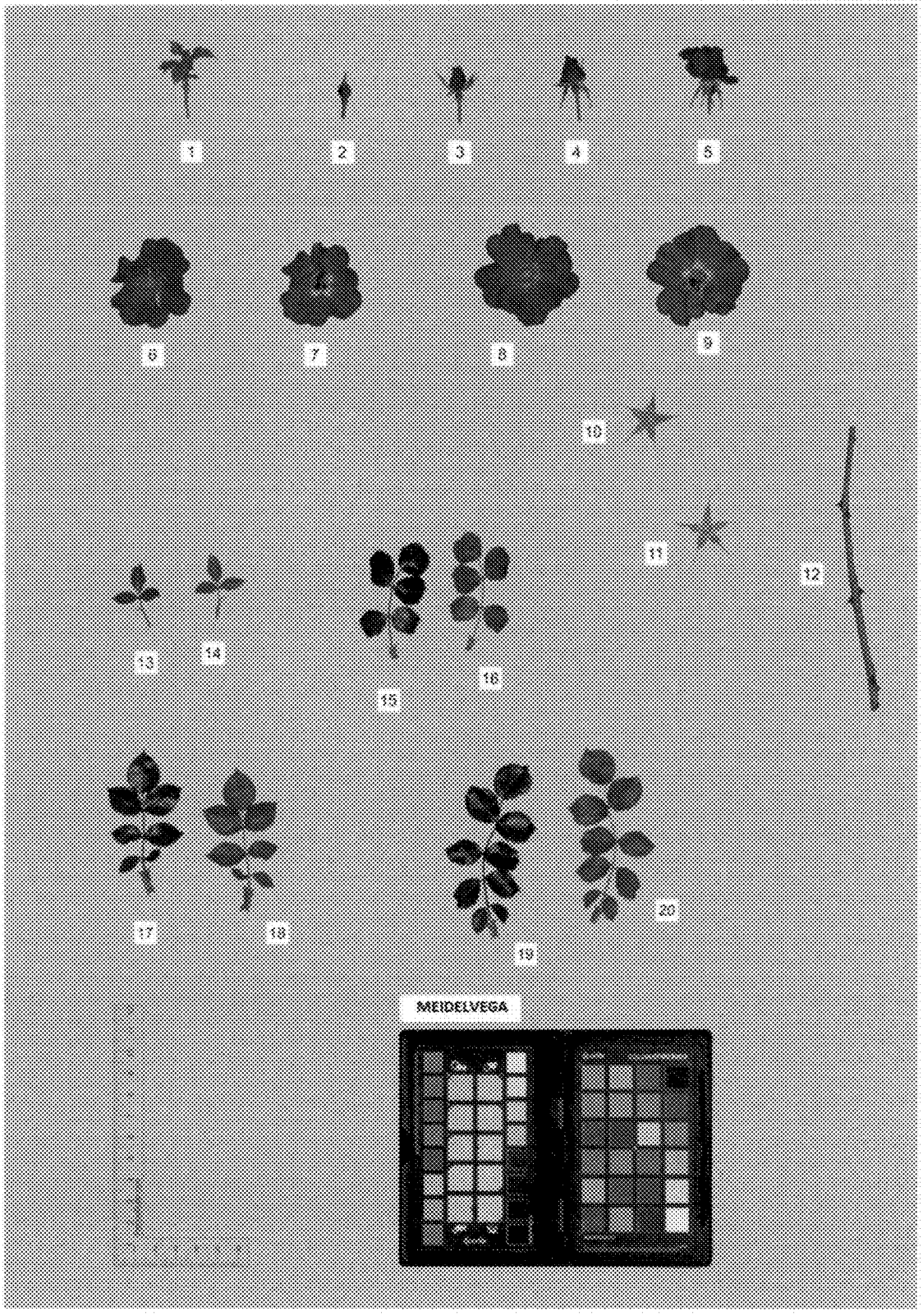
1
2
3
4
5
6
7
8
9
10
11
12
13
14
15
16
17
18
19
20
MEIDELVEGA